US009468488B2

(12) United States Patent
Bates et al.

(10) Patent No.: US 9,468,488 B2
(45) Date of Patent: Oct. 18, 2016

(54) THERMO-CHEMICAL MEDICAL DEVICE FOR MANIPULATION OF TISSUE

(75) Inventors: Brian L. Bates, Bloomington, IN (US); Jeffry S. Melsheimer, Springville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1040 days.

(21) Appl. No.: 13/581,386

(22) PCT Filed: Feb. 28, 2011

(86) PCT No.: PCT/US2011/026460
§ 371 (c)(1),
(2), (4) Date: Aug. 27, 2012

(87) PCT Pub. No.: WO2011/109288
PCT Pub. Date: Sep. 9, 2011

(65) Prior Publication Data
US 2012/0323213 A1 Dec. 20, 2012

Related U.S. Application Data

(60) Provisional application No. 61/309,081, filed on Mar. 1, 2010.

(51) Int. Cl.
*A61B 18/06* (2006.01)
*A61B 18/00* (2006.01)

(52) U.S. Cl.
CPC ...... *A61B 18/06* (2013.01); *A61B 2018/00023* (2013.01)

(58) Field of Classification Search
CPC .......... A61B 2018/00005; A61B 2018/00011;
A61B 2018/00023; A61B 2018/00041;
A61B 2018/00095; A61B 2018/00166;
A61B 2018/00577; A61B 2018/044; A61B 2018/046; A61B 18/04; A61B 18/06
See application file for complete search history.

(56) References Cited

U.S. PATENT DOCUMENTS 203,387 A 5/1878 Stohlmann et al.
319,698 A 6/1885 Graefe
(Continued)

FOREIGN PATENT DOCUMENTS

WO WO 83/03961 A1 11/1983
WO WO 01/68160 A1 9/2001
(Continued)

OTHER PUBLICATIONS

Non-Final Office Action from U.S. Appl. No. 12/914,167, Dated Dec. 21, 2015.
(Continued)

*Primary Examiner* — Joseph Stoklosa
*Assistant Examiner* — Nicole L Pobre
(74) *Attorney, Agent, or Firm* — Brinks Gilson & Lione

(57) ABSTRACT

The present invention provides a medical device for manipulation of tissue of a patient. The medical device comprises a shaft having a proximal section extending to a distal section that has a closed distal end portion. The shaft has a plurality of lumens formed therein including a first lumen and a second lumen. The first lumen is for distally advancing a first reactant through the proximal section. The second lumen is for distally advancing a second reactant through the proximal section. Positioned longitudinally within the shaft and distally from the first and second lumens is a mixing element. The mixing element is in fluid communication with the first and second lumens. The mixing element has a series of baffles for mixing the first and second reactants together producing a reaction product to heat the closed distal end portion of the shaft for manipulation of the tissue.

9 Claims, 4 Drawing Sheets

(56) References Cited

U.S. PATENT DOCUMENTS

| | | |
|---|---|---|
| 4,631,055 A | 12/1986 | Redl et al. |
| 4,796,622 A | 1/1989 | Lu et al. |
| 4,979,518 A | 12/1990 | Itoh et al. |
| 6,190,380 B1 | 2/2001 | Abela |
| 6,224,591 B1 | 5/2001 | Claren et al. |
| 6,379,378 B1 | 4/2002 | Werneth et al. |
| 6,576,001 B2 | 6/2003 | Werneth et al. |
| 6,824,555 B1 | 11/2004 | Towler et al. |
| 6,832,995 B1 | 12/2004 | Towler et al. |
| 6,905,510 B2 | 6/2005 | Saab |
| 7,097,642 B1 | 8/2006 | Sprague et al. |
| 7,118,591 B2 | 10/2006 | Frank et al. |
| 7,211,066 B1 | 5/2007 | Merrill |
| 7,485,107 B2 | 2/2009 | DiFiore et al. |
| 7,490,738 B2 | 2/2009 | Crews |
| 7,572,257 B2 | 8/2009 | Whayne et al. |
| 2002/0016621 A1 | 2/2002 | Werneth et al. |
| 2002/0049409 A1* | 4/2002 | Noda .................. A61F 7/12 604/113 |
| 2002/0049484 A1 | 4/2002 | Werneth et al. |
| 2004/0005295 A1 | 1/2004 | Lee et al. |
| 2005/0085769 A1 | 4/2005 | MacMahon et al. |
| 2005/0187542 A1 | 8/2005 | Wayne et al. |
| 2006/0253088 A1 | 11/2006 | Chow et al. |
| 2007/0027449 A1* | 2/2007 | Godara .............. A61B 18/1482 606/41 |
| 2007/0167776 A1 | 7/2007 | Kochavi et al. |
| 2007/0173786 A1 | 7/2007 | Recinella et al. |
| 2007/0203479 A1 | 8/2007 | Auth et al. |
| 2008/0103564 A1 | 5/2008 | Burkinshaw et al. |
| 2008/0243112 A1 | 10/2008 | DeNeve |

FOREIGN PATENT DOCUMENTS

| | | | |
|---|---|---|---|
| WO | WO 2008/106357 A1 | 9/2008 | |
| WO | WO 2008106357 A1 * | 9/2008 | ............. A61B 18/06 |

OTHER PUBLICATIONS

Final Office Action from U.S. Appl. No. 12/914,167, Dated Jul. 8, 2015.

Non-Final Office Action from U.S. Appl. No. 12/914,167, Dated Dec. 19, 2014.

Final Office Action from U.S. Appl. No. 12/914,167, Dated Oct. 16, 2013.

Non-Final Office Action from U.S. Appl. No. 12/914,167, Dated Mar. 28, 2013.

Final Office Action from U.S. Appl. No. 12/914,167, Dated Oct. 4, 2012.

Non-Final Office Action from U.S. Appl. No. 12/914,167, Dated Apr. 9, 2012.

* cited by examiner

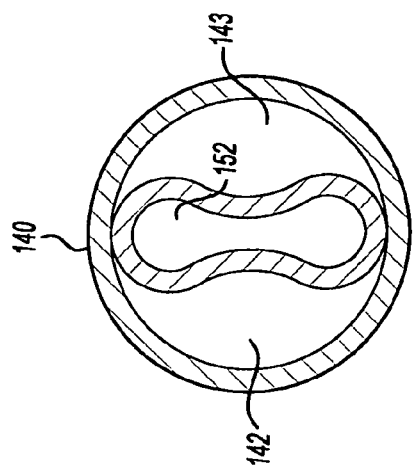
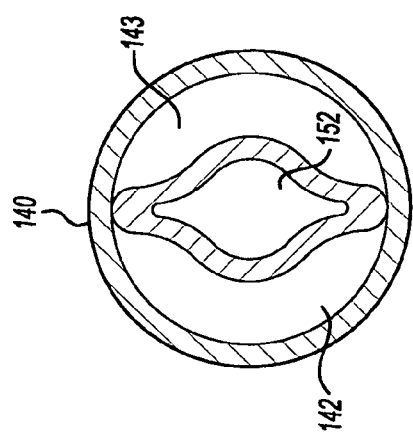
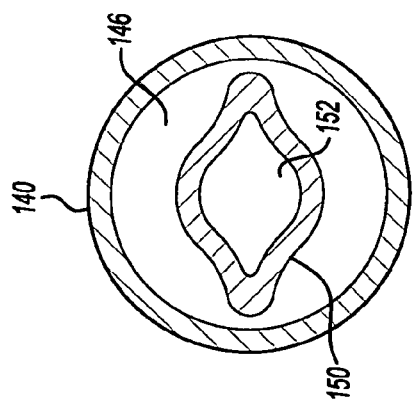
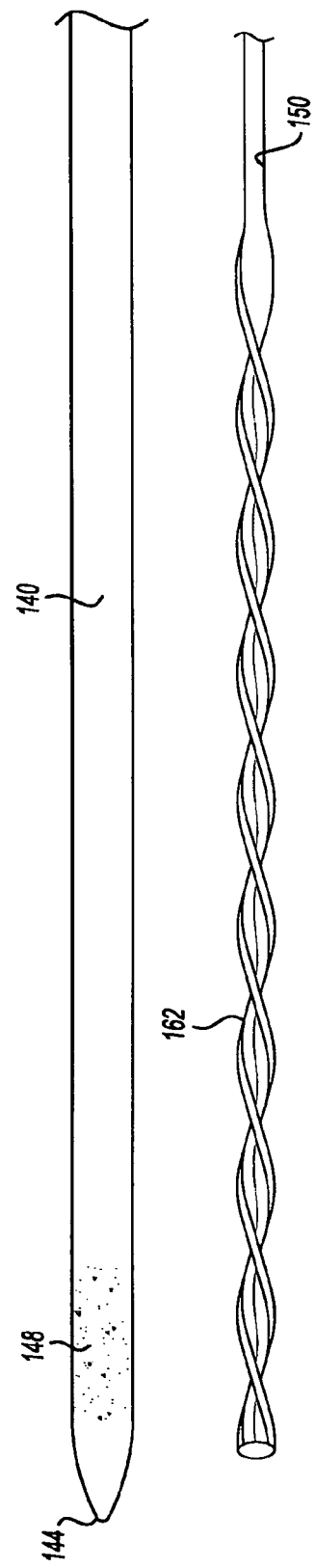
Fig-2B2
Fig-2B1
Fig-2A
Fig-4

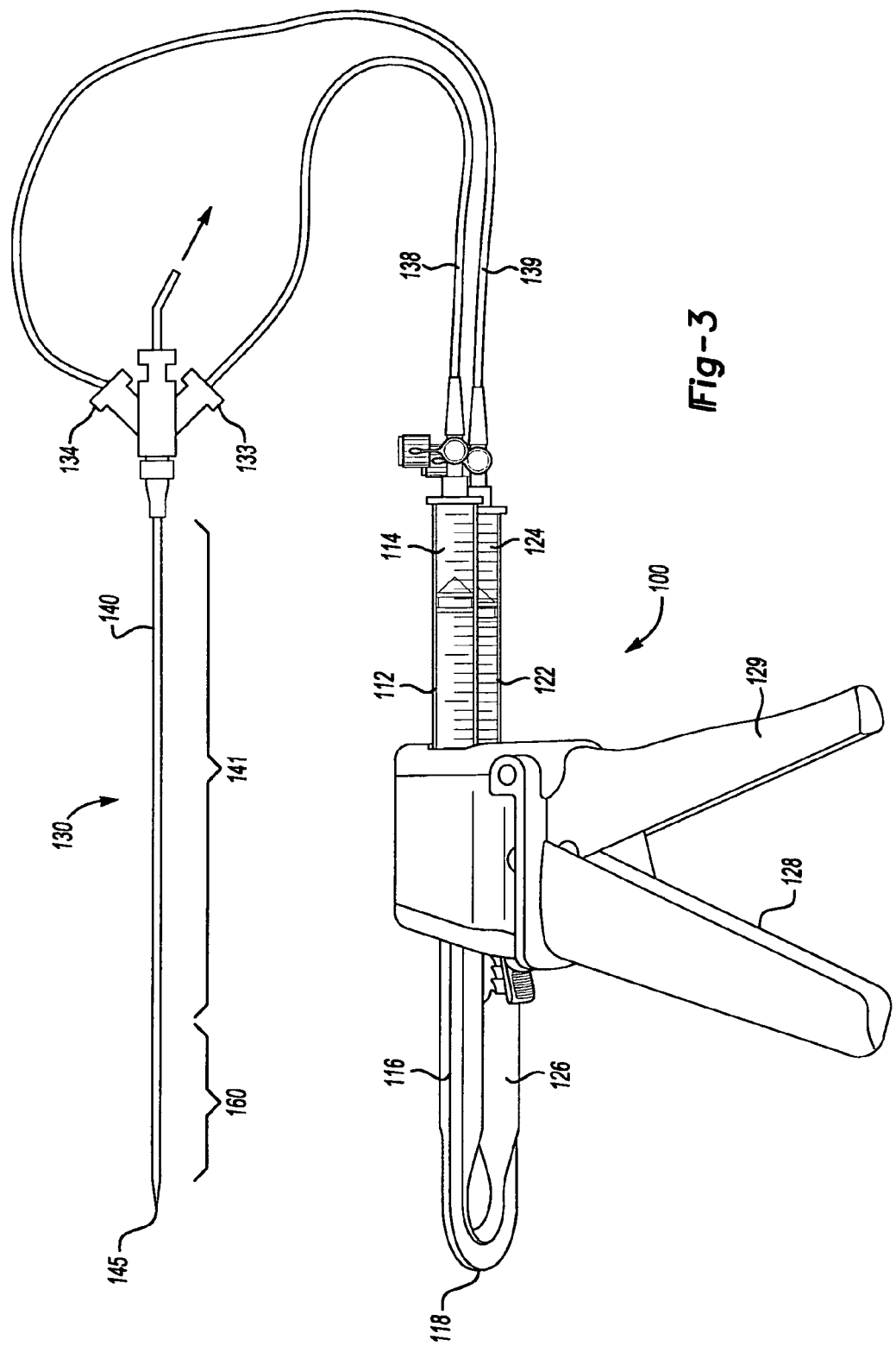

THERMO-CHEMICAL MEDICAL DEVICE FOR MANIPULATION OF TISSUE

CROSS-REFERENCE TO RELATED APPLICATIONS

This application is related to and claims the benefit of priority to PCT/US2011/026460, filed on Feb. 28, 2012, which application claims priority to U.S. Provisional Patent Application Ser. No. 61/309,081, filed Mar. 1, 2010 both of which are incorporated herein by reference in their entirety.

BACKGROUND OF THE INVENTION

1. Field of the Invention

The present invention relates generally to medical devices for tissue manipulation of a patient, such as for example ablation or cauterization, and more specifically to a thermo-chemical medical device that generates heat for tissue manipulation.

2. Background

Several medical applications require the delivery of high local doses of heat for tissue manipulation. For example, tumors, warts, and other non-desirable tissue growths can be treated by the application of heat to a localized site of tissue growth. Sufficient application of heat will cause the death of cells near the localized site of heat release. Typically, the temperature necessary to kill tumor cells is in the range of about 43 degrees Celsius (° C.) to about 47° C., while at the same time the temperature of the normal surrounding tissue should be kept below about 43° C.

Localized heat release, or generation, can be achieved by several means. Some examples of current approaches for heating tissue include: gamma radiation, lasers, ultrasound, microwave, radio frequency waves, and resistant heating.

A significant drawback to each of these methods is that the patient's body is subjected to strong electromagnetic fields and often the surrounding tissue of the targeted treatment location is subjected to radiation or high levels of heat, even when lower doses of treatment are used. This may result in the unintentional killing of normal surrounding tissue cells. Accordingly, further improvements and enhancements are needed for various forms of tissue manipulation, such as for tissue ablation or cauterization.

BRIEF SUMMARY OF THE INVENTION

In satisfying the above need and overcoming the above and other drawbacks and limitations of the known technology, the present invention provides a medical device for tissue manipulation of a patient. The medical device comprises a shaft having a proximal section extending to a distal section that has a closed distal end portion. The shaft has a plurality of lumens formed therein including a first lumen and a second lumen. The first and second lumens are for correspondingly advancing a first reactant and a second reactant distally through the proximal section of the shaft. Positioned longitudinally within the shaft and distally from the first and second lumens is a mixing element which is in fluid communication with the first and second lumens. The mixing element has a series of baffles for mixing the first and second reactants together producing a reaction product to heat the closed distal end portion of the shaft for manipulation of the patient's tissue.

In at least one other embodiment of the present invention, a medical kit for tissue manipulation of a patient is provided. The medical kit comprises a first reservoir configured to contain a first reactant. A second reservoir is configured to contain a second reactant. A medical device as described in the foregoing paragraph is also provided. The first lumen of the shaft of the medical device is in fluid communication with the first reservoir to receive the first reactant and the second lumen is in fluid communication with the second reservoir to receive the second reactant.

In at least one other embodiment of the present invention, a method of using a medical device for manipulation of tissue of a patient is provided. The method comprises advancing a first reactant and a second reactant correspondingly along a first lumen and a second lumen that are formed through a proximal section of a shaft of the medical device. The first and second reactants are mixed together along a series of baffles of a mixing element which is in fluid communication with the first and second lumens. The mixing element is positioned longitudinally within the shaft and distally from the first and second lumens. Mixing of the first and second reactants forms a reaction product that heats a closed distal end portion of the shaft for manipulation of the patient's tissue.

Further objects, features, and advantages of the invention will become apparent from consideration of the following description and the appended claims when taken in connection with the accompanying drawings.

BRIEF DESCRIPTION OF THE DRAWINGS

FIG. 2a is a sectional view of the thermo-chemical medical system depicted in FIG. 1 along line 2a-2a;

FIG. 2b1 is a sectional view of one embodiment of the thermo-chemical medical system depicted in FIG. 1 along line 2b-2b;

FIG. 2b2 is a sectional view of another embodiment of the thermo-chemical medical system depicted in FIG. 1 along line 2b-2b;

FIG. 3 is a perspective view of a thermo-chemical medical system in accordance with another embodiment of the present invention;

FIG. 4 is a partial view of an unassembled distal portion of a thermo-chemical medical system and mixing element in accordance with one embodiment of the present invention;

DETAILED DESCRIPTION OF THE INVENTION

Detailed embodiments of the present invention are disclosed herein. It is understood, however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and for teaching one skilled in the art to practice the present invention.

The present invention seeks to overcome some of the problems associated with various forms of manipulating tissue of a patient, such as for example, ablation of tissue containing tumor cells, etc. or cauterization or repair of damaged tissue. The present invention provides a multi-lumen thermo-chemical medical device configured for advancing two reactants to a mixing element or feature that is positioned distally within the medical device. The two reactants are mixed together along the mixing element, producing an exothermic chemical reaction that heats a closed distal end portion of the medical device to a temperature suitable for manipulating tissue of a patient. The closed distal end portion of the medical device is configured to provide localized heating via conduction to the targeted tissue site without using any strong electromagnetic radiation and preferably with only minimal heating to the surrounding tissue.

Figure 1:
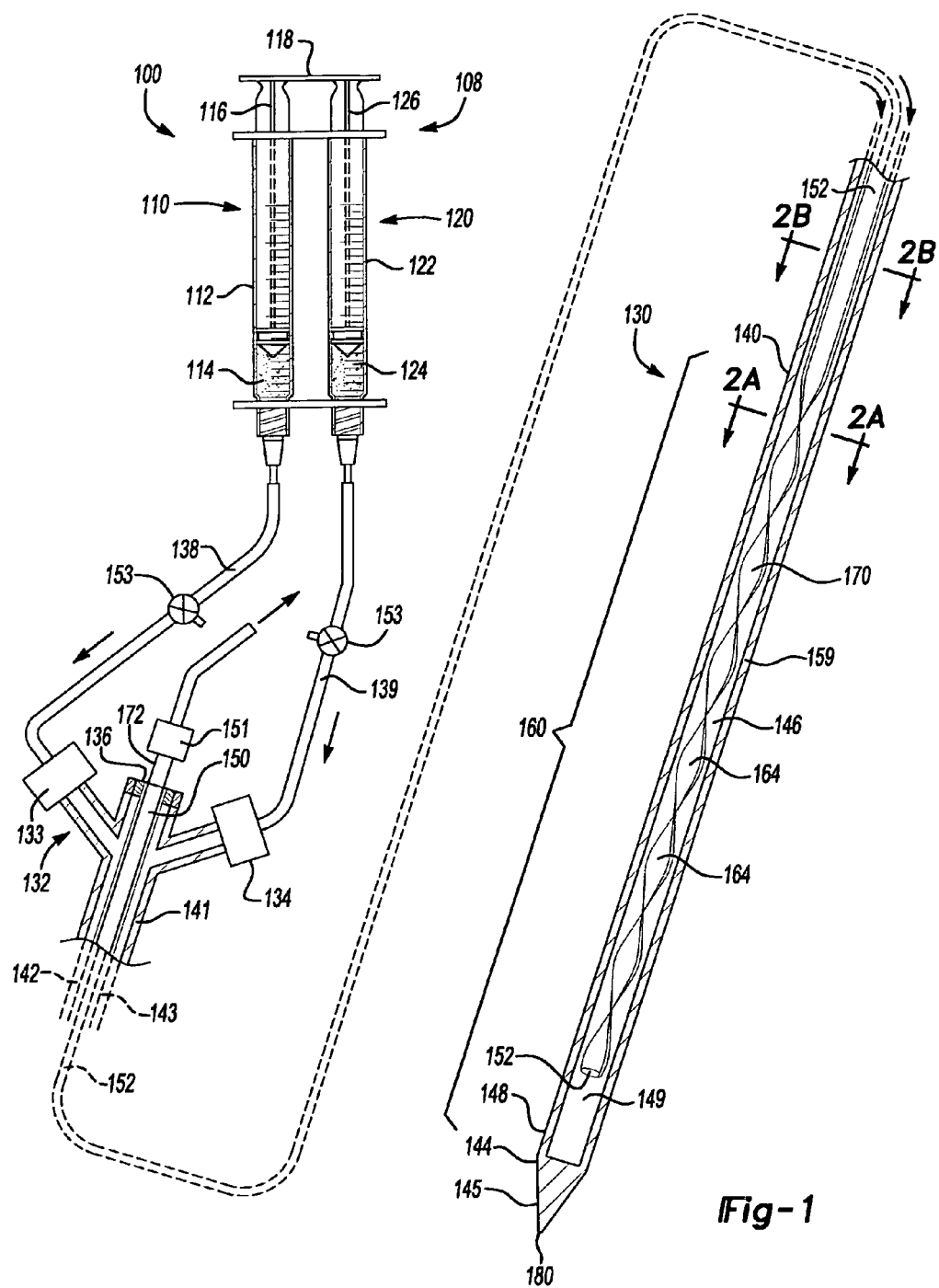
FIG. 1 is a perspective view of a thermo-chemical medical system for manipulation of tissue including a partial sectional view of a multi-lumen mixing device in accordance with an embodiment of the present invention.

Referring now to FIGS. 1-2b2, one embodiment of a thermo-chemical system 100 is illustrated for tissue manipulation of a patient. The medical system 100 includes an infusion system 108 or control handle and a multi-lumen mixing device 130. The infusion system 108 generally includes infusion devices 110 and 120 (e.g. syringes) that have first and second reservoirs 112 and 122 (e.g. barrels of the syringes). The first reservoir 112 contains a first chemical reactant 114 and the second reservoir contains a second chemical reactant 124.

The infusion system 108 has first and second actuators 116 and 126 (e.g. plungers of the syringes) correspondingly disposed in the first and second reservoirs 112 and 122. The first and second actuators 116 and 126 are configured to be movable within the reservoirs 112 and 122. As illustrated, the actuators 116 and 126 are linked together by a coupling 118. The infusion device 108 may be operated by pressing on the coupling 118 to simultaneously advance the first and second actuators distally through the first and second reservoirs 112 and 122, thereby advancing the first and second reactants 114 and 124 from their respective reservoirs 112 and 122 toward the multi-lumen mixing device 130. In this embodiment, the reservoir 112 and 122 may be sized accordingly to preferably ensure that the reactants 114 and 124 are simultaneously advanced into the mixing device 130 at a desired stoichiometric ratio for producing an exothermic chemical reaction. Alternatively, the infusion device 108 may be formed without a coupling 118 so that the actuators 116 and 126 may be moved through their respective reservoirs 112 and 122 independently of each other.

The multi-lumen mixing device 130 generally includes an elongated element in the form of a shaft 140, such as for example, a needle or catheter. The shaft 140 has a plurality of lumens including first and second lumens 142 and 143 formed through its proximal section 141. The shaft also includes a cannula 150 disposed therein that defines a third lumen 152. As illustrated, the cannula 150 is arranged adjacent to and between both the first and second lumens 142 and 143 in a non-concentric relationship. Alternatively, the first and second lumens 142 and 143 can be concentric lumens with the shaft 150 and corresponding third lumen 152 positioned concentrically within the first and second lumens 142 and 143.

At the proximal end of the shaft's proximal section 141, the multi-lumen mixing device 130 includes a hub 132 generally including a first coupling 133, cannula support 136 and a second coupling 134. The first coupling 133 provides access to the first lumen 142 and the second coupling 134 provides access to the second lumen 143. The cannula support 136 supports and secures the cannula 150 within the shaft 140 in a coaxial arrangement with the shaft's central lumen 146 adjacent to the first and second lumens 142 and 143. A cannula coupling 151 provides access to the third lumen 152 of the cannula 150.

A first tube 138 couples the first reservoir 112 to first lumen 142 through the corresponding coupling 133 while a second tube 139 couples the second reservoir 122 to the second lumen 143 through the corresponding coupling 134. As shown, the tubes 138 and 139 are flexible to allow relative movement between the infusion device 108 and the mixing device 130. Alternatively, the tubes 138 and 139 may be rigid or incorporated into a rigid structure so that the infusion device 108 and the mixing device 130 move together.

In the illustrated embodiment, each of the tubes 138 and 139 has an interposed three-way valve 153. The three-way valves 153 may be selectively opened to allow the reservoirs 112 and 122 to be respectively filled with the first and second reactants 114 and 124. This allows the interventionalist to refill the reservoirs 112 and 124 for reusing the infusion device 108 for multiple tissue treatments for example. The infusion device 108 may be provided initially with the first and second reactants 114 and 124 already contained in their corresponding reservoirs 112 and 122 or alternatively, the reservoirs 112 and 122 may be initially empty and the interventionalist can use the three-way valves to fill the reservoirs 112 and 122 with the reactants 114 and 124 prior the administering a tissue treatment to the patient.

In the distal section 159 of the mixing device 130 is a reaction or mixing chamber 160 that generally includes a mixing element 162 and a distal chamber 149 that is positioned distally from the mixing element 162. The mixing element 162 is coaxially disposed in the central lumen 146 of the shaft 140 and distally from the first and second lumens 142 and 143. Adjacent to the distal chamber 149 is a closed distal end portion 144 of the shaft 140 defining a tip 145.

In the illustrated embodiment, the mixing element 162 is configured as a static spiral mixer that includes a series of longitudinally positioned baffles 164. The baffles 164 are configured to disrupt fluid flow over the baffles 164 to promote turbulent flow and mixing of the fluids. In at least one embodiment, the mixing element 162 is formed as a generally planer structure that has a twisted pattern in its longitudinal axis providing a longitudinal spiral that defines the series of baffles 164.

The mixing element 162 can be attached to or integrally formed with cannula 150. As illustrated, the mixing element 162 is integrally formed with cannula 150 (also shown in FIG. 4) where the original length of the cannulated material is substantially flattened to a generally planer condition along its distal end segment 170 and then the planer condition is twisted. The flattened, twisted distal end segment 170 of the cannula 150 has the third lumen 152 formed therethrough and the lumen 152 is open in an unobstructed condition so that fluid communication between the proximal section 172 of the cannula 150 and the distal chamber 149 is maintained. The outer wall of the cannula 150 is integral with the outer wall of the mixing element 162.

As discussed above, the infusion device 108 preferably provides for simultaneous delivery of the first and second reactants 114 and 124 from their respective reservoirs 112 and 122 through movement of the coupling 118 and thereby movement of the actuators 116 and 126. The first and second reactants 114 and 124 are expelled from their reservoirs 112 and 122, where the first reactant 114 is advanced to and through the first lumen 142, and the second reactant 124 is advanced to and through the second lumen 143. In at least one embodiment, the first and second lumens openly terminate at an intermediate portion within the shaft 140 (e.g. proximally of the mixing element 162) so that the lumens 142 and 143 are in fluid communication with the central lumen 146.

Through the continuous movement of the actuators 116 and 126, the first and second reactants 114 and 124 each enter the reaction chamber 160 where the mixing element 162 has the series of baffles 164 that disrupt the flow of the reactants 114 and 124 so as to produce a pattern of mixing to mix the first and second reactants 114 and 124 together. The mixing of the first and second reactants 114 and 124 promotes an exothermic chemical reaction between the first and second reactants 114 and 124 generating heat and producing a reaction product.

After passing along the mixing element 162, the reaction product and/or any unreacted reactants 114 and 124 enter the distal chamber 149. The distal chamber 149 may provide additional time for the reactants 114 and 124 to comingle before being expelled proximally therefrom through the third lumen 152 of the cannula 150 for removal of the reaction product from the multi-lumen mixing device 130. The relative length and diameter of the distal chamber 149 can be configured to provide an adequate or predetermined delay period for permitting the chemical reaction to generate a desired amount of heat before the reaction product is expelled from the multi-lumen mixing device 130. At least a portion of the chemically generated heat in the distal chamber 149 is conducted through the closed distal end portion 144 of the shaft 140 so that the tip 145 reaches a sufficiently high temperature for manipulating tissue. This arrangement of supplying the reactants 114 and 124 through the first and second lumens 142 and 143 and along the mixing element 160 to the distal chamber 149 to produce the reaction product and generate heat, and then removal of the reaction product from the distal chamber 149 through the third lumen 152 for removal from the mixing device 130, provides a continuous flow reactor system where the temperature of the closed distal end portion 144 can be repeatably and predictably controlled while controlling the flow rate of the reactants 114 and 124 through the mixing device 130.

The device's tip 145 can be configured in several different ways. In one embodiment, the tip 145 includes a cutting and/or burrowing feature 180 on the distal-most end permitting the shaft to be inserted directly into tissue such as skin, organs, arteries, veins and bone. For example, the tip 145 may include a double cutting edge, a saw-tooth cutting edge, a pointed end, a trocar tip, or any other suitable configuration desired for cutting and/or burrowing into tissue. In another embodiment, the tip 145 may be blunt, permitting the shaft to be inserted into an artery or venous structure and to be advanced therethrough to a tissue site that is targeted for treatment. Such an embodiment generally requires a separate introducer as is known in the art for percutaneous procedures and for venous or arterial access.

The tip 145 preferably has a relatively low mass to facilitate rapid heating of the tip 145. The tip 145 is also preferably constructed of a material with a relatively high thermal conductivity and/or thermal diffusivity such as a metal, e.g., stainless steel material including but not limited to 302, 304 or 316 series stainless steel, Nitinol (a superelastic nickel-titanium alloy), nickel, chromium or MP35N for example. A relatively high thermal conductivity material and more specifically, a relatively high thermal diffusivity material will further facilitate rapid heating of the tip 145 for tissue manipulation. Alternatively, the tip 145 may be made of a plastic including a filled reinforced plastic, or any other suitable rigid or flexible material known to those skilled in the art.

In this regard, the elongated shaft 140, cannula 150 and mixing element 162 can be constructed of either rigid or flexible materials. In embodiments in which the multi-lumen mixing device 130 is configured as a needle with a cutting/burrowing feature on the tip 145 to provide direct access to body tissue, then the shaft 140 can be made of a rigid material such as metal or a relatively rigid polymer. In other embodiment in which the multi-lumen mixing device 130 is configured as a catheter to be introduced through arterial or venous access into the body cavity through a laparoscopic method, then the shaft 140, mixing element 162 and cannula 150 may be constructed from a flexible material such as a relatively flexible polymer or flexible metal material. As examples, the shaft 140, cannula 150, and mixing element 162 can be constructed from metals such as stainless steel material including but not limited to 302, 304 or 316 series stainless steel, Nitinol, nickel, chromium or MP35N, and/or from polymeric materials such as silicone, polyethylene terephthalate, polyurethane, polyamide, polyester, or any other suitable material known to those skilled in the art.

In one embodiment, an interventionalist may manually apply a forced to the coupling 118 to contemporaneously move the actuators 116 and 126 to simultaneously deliver the first and second reactants 114 and 124 to the multi-lumen mixing device 130 through the corresponding tubes 138 and 139. In other embodiments, the interventionalist may selectively activate a computer controlled mechanism that acts upon the coupling 118 to move the actuators 116 and 126. In yet another embodiment, the reservoirs 112 and 122 may not be physically coupled to one another and the actuators 116 and 126 may be separately adjusted to dispense the first and second reactants 114 and 124 simultaneously or in a selected sequence. For example, individual infusion pumps could replace the linked infusion devices 110 and 120 and in yet another embodiment, the actuators 116 and 126 may be pulsed relative to one another to provide different mixing dynamics within the multi-lumen mixing device 130.

Furthermore, if the interventionalist wishes to discontinue or interrupt a tissue manipulation procedure, the flow of the reactants 114 and 124 to the multi-lumen mixing device 130 may be stopped by ceasing movement of the actuators 116 and 126 through the reservoirs 112 and 124. The formation of new reaction product will thereby cease, terminating further heat generation in the distal chamber 149 and allowing the relatively low mass closed end portion 144 to quickly cool. The flow of the reactants 112 and 124 to the mixing device 130 may then be reactivated as needed to complete the procedure.

Referring to FIG. 4, the multi-lumen mixing device 130 may include visualization markers 148 near or on the closed distal end portion to provide enhanced visualization during insertion and use. For example, when utilizing ultrasonic visualization techniques, the visualization markers 148 could comprise an echogenic marker such as a series of small dimple-like indentations on the outer surface of the elongated element 140, for example those used in ECHOTIP™ echogenic needles available from Cook Medical, Bloomingham, Ind., USA, to provide enhanced ultrasonic return. In other embodiments, a radio-opaque marker can be used to enhance x-ray response during fluoroscopic or other x-ray visualization technique. The visualization markers 140 may improve the ability of the interventionalist to monitor the position of the tip 145 within the patient's body during use.

Referring to FIG. 3, one embodiment of the system 100 is illustrated including the reservoirs 112 and 122 containing the first and second reactants 114 and 124, and the actuators 116 and 126 coupled by the coupling 118. The actuators 116 and 126 and the reservoirs 112 and 122 are held in an injector 128 that is configured as a control handle and capable of simultaneously moving the actuators 116 and 126 by manually actuating a trigger grip 129. The reservoirs 112 and 122 are coupled through the tubing 138 and 139 to the multi-lumen mixing device 130 through the couplings 133 and 134. In the illustrated embodiment, the multi-lumen mixing device 130 is comparatively rigid with a needle like catheter 140 including a pointed end tip 145.

Figures 5, 6:
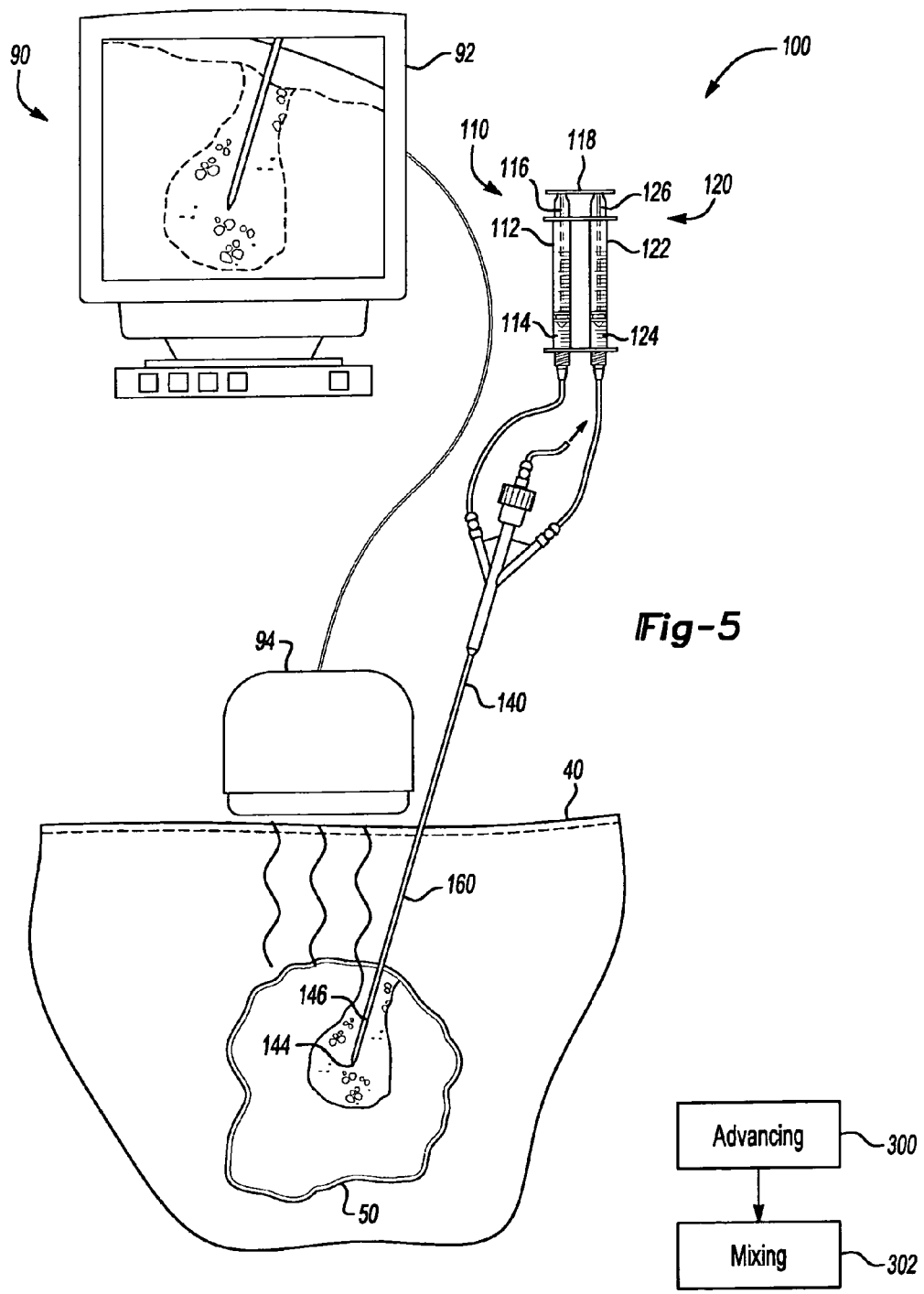
FIG. 5 illustrates a thermo-chemical medical system configured as an ablation system including an ultrasonic imaging system in accordance with one embodiment of the present invention.
FIG. 6 is a flow chart of a method for using a medical device for manipulation of tissue of a patient in accordance with one example of the present invention.

Referring to FIG. 5, one embodiment of the system 100 is illustrated as constructed and arranged for use as a thermo-chemical ablation device. In general, the thermo-chemical ablation device generates heat at the closed distal end portion 144 through an exothermic chemical reaction with the first and second reactants 114 and 124. Generally illustrated, the multi-lumen mixing device 130 is inserted into target tissue 50 under the skin 40 of the patient. In this embodiment, the first and second reactants 114 and 124 are selected to react and generate an exothermic chemical reaction. Utilized in this way, the resulting reaction product heats the closed distal end portion 144, which is in contact with the target tissue 50, via the exothermic chemical reaction.

The heat generator from the chemical reaction of the combined first and second reactants 114 and 124 is sufficient to heat the closed distal end portion 144 to ablate at least a portion of the tissue 50 surrounding the end portion 144. The thermal ablation reactants 114 and 124 can be selected to provide suitable energy. In some embodiments, the first reactant 114 may comprise an acid. For example, an acid comprising acetic acid, peracetic acid, hydrochloric acid, hydrobromic acid, hydriodic acid, sulfuric acid, nitric acid, nitrous acid, perchloric acid, phosphoric acid, oxalic acid, pyruvic acid, malonic acid, amino acids, carboxylic acid derivatives or mixtures thereof. Similarly, the second reactant 124 may comprise a base. For example, a base comprising KOH, NaOH, $NH_4OH$, $Ca(OH)_2$, $NaHCO_3$, BuLi, NaOEt, NaSEt, Na or K salts of alkoxides or mixtures thereof.

In one embodiment, the first and second reactants 114 and 124 are selected to form a reaction product that releases heat and comprises salt and water preferably to form a harmless neutral solution. For example, the first and second reactants 114 and 124 may correspondingly comprise an acid and a base where the concentration of the acid and the base are such so as to fully neutralize each other after the thermo-chemical ablation reaction resulting in a reaction product having a pH in the range of about 6 to 8, desirably about 7.

Still referring to FIG. 5, some embodiments of the system 100 may include the use of a medical imaging system 90 to provide real-time monitoring of the multi-lumen mixing device 130 during its insertion and delivery of the reactants 114 and 124. For example, the medical imaging system 90 could include an ultrasonic imaging device to enable the interventionalist to view the distal portion of the multi-lumen mixing device 130 in the target tissue 50. The imaging system 90 may include a probe 94 such as the illustrated ultrasonic probe. The probe 94 can be manipulated on the outside of the patient's body or within a body cavity to provide imaging of the target tissue 50 and/or the multi-lumen mixing device 130. The probe 94 may be connected to a display system 92 that interprets the signal from the probe 94 and generates a display of the targeted portion of the patient's body. In other embodiments, the imaging system 90 could include a fluoroscope, a CT imaging system or the alike.

Referring to FIG. 6 is an example of a method for using a medical device for manipulation of tissue of a patient. The method comprises advancing at 300 a first reactant and a second reactant correspondingly along a first lumen and a second lumen that are formed through a proximal section of a shaft of the medical device. The first and second reactants are mixed together at 302 along a series of baffles of a mixing element that is in fluid communication with the first and second lumens. The mixing element is positioned longitudinally within the shaft and distally from the first and second lumens to form a reaction product to heat a closed distal end portion of the shaft for manipulation of the tissue.

As a person skilled in the art will readily appreciate, the above description is meant as an illustration of the implementation of the principles of the invention. This description is not intended to limit the scope for application of this invention in that the invention is susceptible to modification, variation, and change, without departing from the spirit of this invention as defined in the following claims.

The invention claimed is:

1. A medical device for manipulation of tissue of a patient, the medical device comprising:
   a shaft having a proximal section extending to a distal section that has a closed distal end portion, the shaft having a plurality of lumens formed therein including a first lumen for distally advancing a first reactant through the proximal section and a second lumen for distally advancing a second reactant through the proximal section; and
   a cannula passed through the shaft adjacent to the first and second lumens, the cannula having an outer wall, the cannula defining a longitudinal axis therethrough, the cannula comprising a flattened distal portion, the distal portion being twisted such that the outer wall forms a mixing element positioned longitudinally within the shaft and distally from the first and second lumens, the cannula comprising a third lumen therethrough, the third lumen being coincident with the longitudinal axis throughout the distal portion, the mixing element in fluid communication with the first and second lumens and having a series of baffles for mixing the first and second reactants together producing a reaction product to heat the closed distal end portion of the shaft for manipulation of the tissue.

2. The medical device according to claim 1 wherein the series of baffles are configured as longitudinally twisted elements.

3. The medical device according to claim 1 wherein the third lumen fluidly communicates the reaction product away from the closed distal end towards the proximal section for removal from the shaft.

4. The medical device according to claim 1 wherein the shaft has a distal chamber formed in the distal section adjacent the closed distal end, the distal chamber in fluid communication with the mixing element to receive the reaction product for transferring heat to the closed distal end portion.

5. The medical device according to claim 4 wherein the baffles of the mixing element are disposed in the distal section of the shaft proximally from the distal chamber.

6. The medical device of claim 4, wherein the shaft comprises a central lumen distal of the first and second lumens, the mixing element being disposed within the central lumen, the central lumen being proximal of the distal chamber.

7. The medical device according to claim 1 wherein the mixing element is a static mixer.

8. The medical device according to claim 1 wherein the shaft has an outer distal portion which has one of echogenic or radiopaque features for imaging to facilitate positioning of the shaft within the patient.

9. The medical device according to claim 1 wherein the closed distal end portion is configured to include one of a bevel cutting edge, a saw-toothed cutting edge, a pointed end, a tocar tip or a blunt end for manipulation of the tissue.

\* \* \* \* \*